United States Patent
Zhao et al.

(10) Patent No.: US 10,112,976 B2
(45) Date of Patent: Oct. 30, 2018

(54) PROCESS FOR THE PRODUCTION OF D-ARGINYL-2,6-DIMETHYL-L-TYROSYL-L-LYSYL-L-PHENYLALANINAMIDE

(71) Applicant: Flamma S.P.A., Chignolo D'isola (BG) (IT)

(72) Inventors: Xinjun Zhao, Dalian (CN); Minyu Zheng, Dalian (CN); Xiaozhong Yu, Shenyang (CN); Hanrong Gao, Dalian (CN); Fabrice Cornille, Buress sur Yvette (FR)

(73) Assignee: FLAMMA S.P.A., Chignolo D'Isola (IT)

( * ) Notice: Subject to any disclaimer, the term of this patent is extended or adjusted under 35 U.S.C. 154(b) by 35 days.

(21) Appl. No.: 15/319,917

(22) PCT Filed: Jun. 24, 2015

(86) PCT No.: PCT/EP2015/064303
§ 371 (c)(1),
(2) Date: Dec. 19, 2016

(87) PCT Pub. No.: WO2016/001042
PCT Pub. Date: Jan. 7, 2016

(65) Prior Publication Data
US 2017/0152289 A1  Jun. 1, 2017

Related U.S. Application Data

(60) Provisional application No. 62/019,050, filed on Jun. 30, 2014.

(51) Int. Cl.
*C07K 5/11* (2006.01)
*C07K 5/087* (2006.01)
*C07K 5/068* (2006.01)

(52) U.S. Cl.
CPC ........ *C07K 5/1019* (2013.01); *C07K 5/06086* (2013.01); *C07K 5/0812* (2013.01)

(58) Field of Classification Search
CPC ............ C07K 5/06034; C07K 5/06086; C07K 5/0812; C07K 5/1019
See application file for complete search history.

(56) References Cited

U.S. PATENT DOCUMENTS 9,982,014 B2 *  5/2018  Hirai ............... C07K 5/1021
2007/0249013 A1 * 10/2007  Hibert ............... C07K 5/0817
                                                                435/34
2017/0129920 A1 *  5/2017  Zhao ............... C07K 5/06034

FOREIGN PATENT DOCUMENTS

| EP | 0190597 A2 | 8/1986 |
| WO | 2007027742 A2 | 3/2007 |
| WO | 2013086020 A1 | 6/2013 |
| WO | 2015060462 A1 | 4/2015 |
| WO | 2015100376 A1 | 7/2015 |

OTHER PUBLICATIONS

Reddy et al. Synthesis and Pharmacological Evaluation of Highly Potent [Dmt1]DALDA Analogs. Adv Exp Med Biol. 2009 ; 611: 473-474. (Year: 2009).*
Search Report and Written Opinion of PCT/EP2015/064303 of Sep. 14, 2015.

* cited by examiner

*Primary Examiner* — Marcela M Cordero Garcia
(74) *Attorney, Agent, or Firm* — Silvia Salvadori, P.C.; Silvia Salvadori

(57) ABSTRACT

The invention relates to a process for solution-phase synthesis of D-Arginyl-2,6-dimethyl-L-tyrosyl-L-lysyl-L-phenylalaninamide, an active ingredient used for both common and rare diseases including a mitochondrial targeted therapy for ischemia reperfusion injury.

12 Claims, No Drawings

PROCESS FOR THE PRODUCTION OF D-ARGINYL-2,6-DIMETHYL-L-TYROSYL-L-LYSYL-L-PHENYLALANINAMIDE

This application is a U.S. national stage of PCT/EP2015/064303 filed on 24 Jun. 2015, which claims priority to and the benefit of U.S. Provisional Application Ser. No. 62/019,050 filed on 30 Jun. 2014, the contents of which are incorporated herein by reference in their entireties.

TECHNICAL FIELD

The invention relates to a process for solution-phase synthesis of D-Arginyl-2,6-dimethyl-L-tyrosyl-L-lysyl-L-phenylalaninamide (abbreviated H-D-Arg-(2,6-Dimethyl)Tyr-L-Lys-L-Phe-NH$_2$, development code SS-31, MTP-131, RX-31) of Formula (I), an active ingredient developed by Stealth BioTherapeutics under the investigational drug brand names Bendavia® and Ocuvia®, for both common and rare diseases including a mitochondrial targeted therapy for ischemia reperfusion injury.

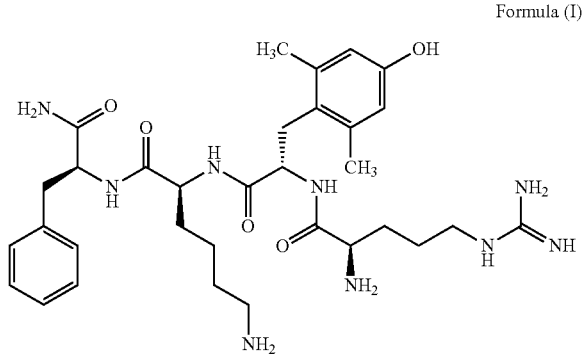 [SMILES: Cc1cc(O)cc(C)c1C[C@H](NC(=O)[C@H](N)CCCNC(=N)N)C(=O)N[C@@H](CCCCN)C(=O)N[C@@H](Cc1ccccc1)C(N)=O]

Formula (I)

BACKGROUND

The product belongs to the class of so-called "Szeto-Schiller peptides". Szeto-Sciller peptides or "SS peptides" are small, aromatic-cationic, water soluble, highly polar peptides, such as disclosed in U.S. Pat. No. 6,703,483 and U.S. Pat. No. 7,576,061, which can readily penetrate cell membranes. The aromatic-cationic peptides include a minimum of two amino acids, and preferably include a minimum of four amino acids, covalently joined by peptide bonds. The maximum number of amino acids is about twenty amino acids covalently joined by peptide bonds. As described by EP 2012/2436390, optimally, the number of amino acids present in the SS peptides is four.

Bendavia® is being tested for the treatment of ischemia reperfusion injury in patients with acute myocardial infarction (AMI), for the treatment of acute kidney injury (AKI) and renal microvascular dysfunction in hypertension, for the treatment of skeletal muscle dysfunction, for the treatment of mitochondrial myopathy and for the treatment of chronic heart failure. Trials are ongoing to assess the Ocuvia's potential to treat Leber's Hereditary Optic Neuropathy (LHON) a devastating inherited disease that causes sudden blindness, often in young adults.

Mitochondria are the cell's powerhouse, responsible for more than 90% of the energy our bodies need to sustain life and support growth. The energetics from mitochondria maintains healthy physiology and prevents disease. In many common and rare diseases, dysfunctional mitochondria are a key component of disease progression.

D-Arginyl-2,6-dimethyl-L-tyrosyl-L-lysyl-L-phenylalaninamide is a cell-permeable and mitochondria-targeted peptide that showed antioxidant activity and was concentrated in the inner mitochondrial membrane. Compound (<1 nM) significantly reduced intracellular reactive oxygen species, increased mitochondrial potential and prevented tBHP-induced apoptosis in both N2A and SH—SY5Y neuronal cell lines. In rats, intraperitoneal treatment (1 and 3 mg/kg) 1 day prior to unilateral ureteral obstruction and every day thereafter for 14 days significantly decreased tubular damage, macrophage infiltration and interstitial fibrosis. Compound (3 mg/kg i.p. qd for 2 weeks) also prevented apoptosis and insulin reduction in mouse pancreatic islets caused by streptozotocin.

Further studies performed in a G93A mouse model of amyotrophic lateral sclerosis (ALS) demonstrated that the compound (5 mg/kg/day i.p. starting at 30 days of age) led to a significant delay in disease onset. Potentially useful for the treatment of ALS and may be beneficial in the treatment of aging and diseases associated with oxidative stress.

In the last few years the peptide H-D-Arg-(2,6-Dimethyl)Tyr-L-Lys-L-Phe-NH$_2$, shown in FIG. 1, and its therapeutic activity have been disclosed and claimed by in several patent applications.

EP 2436390, US 20110245182 and US 20110245183 claim topical anesthetic compositions for application to the skin for pain management or anti-skin aging agents, respectively, comprising Szeto-Schiller peptides; SS-31 is specifically claimed as active ingredient. Sequence of solid-phase synthesis is indicated as the preferred preparation process.

U.S. Pat. No. 7,718,620 claims a process of treating or preventing ischemia-reperfusion injury of the kidney in a mammal by administrating an effective amount of an aromatic-cationic peptide. SS-31 is specifically claimed as active ingredient.

WO2005/001023 discloses a generic method and carrier complexes for delivering molecules to cells comprising a molecule and an aromatic cationic peptide of type D-Arg-Dmt-Lys-Phe-NH$_2$. The tetrapeptide SS-31 is specifically claimed as product useful for the process at claim 18.

WO2012/174117 and WO2014/210056 claim therapeutic compositions based on SS peptides and the aromatic-cationic peptide D-Arg-Dmt-Lys-Phe-NH$_2$ as active agent.

WO 2013/086020, WO 2004/070054 and WO 2005/072295 provide processes for preventing mitochondrial permeability transition and reducing oxidative damage in a mammal, a removed organ, or a cell in need thereof and specifically claims the process wherein the peptide does not have mu-opioid receptor agonist activity, i.e., D-Arg-Dmt-Lys-Phe-NH$_2$.

WO 2009/108695 discloses a process for protecting a kidney from renal injury which may be associated with decreased or blocked blood flow in the subject's kidney or exposure to a nephrotoxic agent, such as a radiocontrast dye. The processes include administering to the subject an effective amount of an aromatic-cationic peptide to a subject in need thereof and one of the selected peptide is D-Arg-Dmt-Lys-Phe-NH$_2$.

U.S. Pat. No. 6,703,483 discloses a detailed procedure for the preparation of novel analogs of DALDA [H-Tyr-D-Arg-Phe-Lys-NH$_2$], namely H-Dmt-D-Arg-Phe-Lys-NH$_2$ using the solid-phase techniques and p-methylbenzhydrylamine resin and protocols that have been extensively used by inventor's laboratory.

Most prior art processes for preparing the compound typically comprise conventionally performed peptide solid-phase synthesis with further purification by chromatography in order to obtain the requested purity for therapeutic use.

It is well known that solid-phase synthesis followed by chromatographic purification is time consuming, very expensive and very difficult to be scaled up on industrial scale, so the need of developing a process for large scale production is obvious. The compound is isolated as organic acid salt, as acetate or trifluoro acetate.

Reddy et al., *Adv. Exp. Med. Biol.*, 2009, 611, 473 generally describe the liquid-phase synthesis of antioxidant peptides of FIG. 1 and similar others (SS-02, SS-20), involving routinely used side chain protecting groups for amino acid building blocks. The guanidine group was protected with $NO_2$ and the $\varepsilon$-$NH_2$ of Lys was protected by Cbz or 2-Cl-Cbz. These peptides were synthesized using Boc/Cbz chemistry and BOP reagent coupling. Starting with the C-terminal Lys residue protected as H-Lys(2-Cl-Cbz)-$NH_2$, (prepared from the commercially available Boc-Lys(2-Cl-Cbz)-OH in two steps by amidation with $NH_4HCO_3$ in the presence of DCC/HOBt following a literature procedure [Ueyama et all, *Biopolymers*, 1992, 32, 1535, PubMed: 1457730], followed by exposure to TFA). Selective removal of the 2-Cl-Cbz in the presence of the $NO_2$ group was accomplished using catalytic transfer hydrogenolysis (CTH) [Gowda et al., *Lett. Pept. Sci.*, 2002, 9, 153].

A stepwise procedure by standard solution peptide synthesis for preparation of potent μ agonist [Dmt]DALDA and its conversion into a potent δ antagonist H-Dmt-Tic-Phe-Lys(Z)—OH by substitution of D-Arg with Tic to enhance the δ opioid agonist activity is described by Balboni et al., *J. Med. Chem.*, 2005, 48, 5608]. A general synthetic procedure for a similar tetrapeptide ([Dmt-D-Arg-Phe-Lys-$NH_2$ is described by Ballet et al., *J. Med. Chem.* 2011, 54, 2467].

Similar DALDA analog tetrapeptides were prepared by the manual solid-phase technique using Boc protection for the α-amino group and DIC/HOBt or HBTU/DIEA as coupling agent [Berezowska et al., *J. Med. Chem.*, 2009, 52, 6941; Olma et al., *Acta Biochim. Polonica*, 2001, 48, 4, 1121; Schiller at al., *Eur. J. Med. Chem.*, 2000, 35, 895.

Despite the high overall yield in the solid-phase approach, it has several drawbacks for the scale-up process such as:
 a. use of the highly toxic and corrosive hydrogen fluoride for cleavage of the peptide from the resin,
 b. low loading (0.3-0.35 mmol/g of resin) proved necessary for successful end-step, and
 c. use of excess amounts of reagents (3-fold of DIC, 2.4-fold of HOBt, etc.) on each step [Ryakhovsky et al., Beilstein J. Org. Chem., 2008, 4(39), 1, doi: 10.376/bjoc.4.39]

SUMMARY

The invention relates to a more efficient process avoiding either solid-phase synthesis or chromatographic purification, more suitable for large scale production. The process of the invention is described in Scheme A.

The following abbreviations are used:
Dmt=2,6-dimethyl tyrosine; Z=benzyloxycarbonyl; $MeSO_3H$=methanesulphonic acid; Boc=Tert-butyloxycarbonyl; NMM=N-methyl morpholine; TB TU=N,N,N',N'-Tetramethyl-O-(benzotriazol-1-yl)uronium tetrafluoroborate; DMF=dimethylformamide; TFA=trifluoroacetic acid.

Scheme A shows the process for the solution phase synthesis of the peptide of Formula 1 was by assembly of the tetrapeptide backbone using O-Benzyl (Bzl) group and benzyloxycarbonyl (Z) group respectively, as the temporary protection for amino acids' N-termini (Scheme FIG. 2), followed by a final catalytic hydrogenolysis. The final product is isolated as organic acid salt, for example, acetic acid salt.

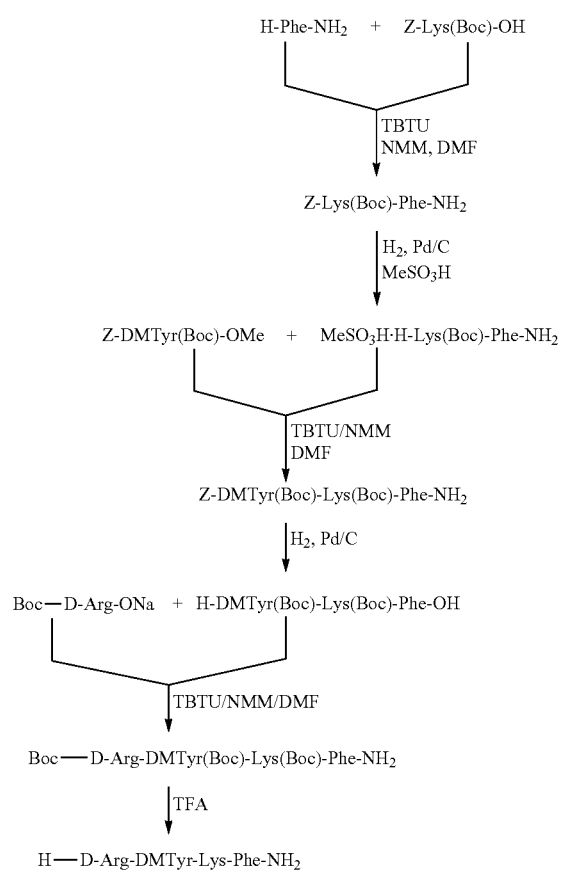

Scheme A

This process is a notable improvement over the prior art and its advantages can be summarized as follows:
 The synthesis is performed in liquid phase allowing the scale up on industrial scale without need of special equipment;
 The selection of the protecting group in the building blocks allows a straightforward synthesis with very simple deprotection at each step and minimize the formation of undesired by-product;
 Each intermediate can be crystallized allowing removal of impurities which are not transferred to the following step;
 The purity of each intermediate is very high and usually close to 99%.

DETAILED DESCRIPTION

The present invention provides, in a first aspect, a novel, efficient process that provides a SS-31 salt, especially the acetic acid salt, which is convenient for the industrial scale and provides the desired product in good yields. In particular, the inventors found that SS-31 acetate salt can be advantageously obtained with a process, in which the overall deprotection step is the n−1 step of the process.

Accordingly, it is an object of the present invention to provide a process for preparing H-D-Arg-Dmt-Lys-Phe-NH$_2$ of formula (I) as the trifluoroacetic acid salt

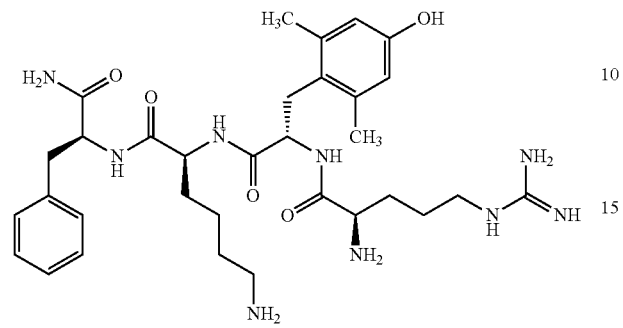

(I)

which comprises the steps of:

coupling compound (II) H-Phe-NH$_2$:

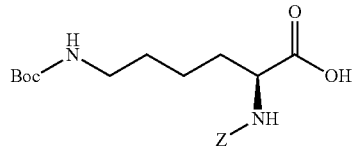

(II)

with compound (III) Z-Lys(Boc)-OH:

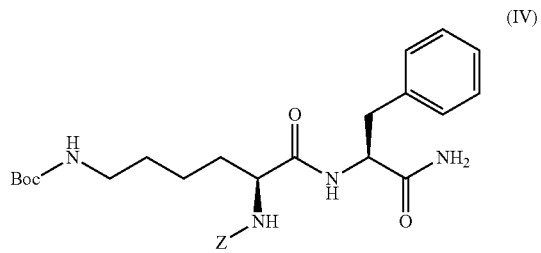

(III)

to obtain a compound of formula (IV), Z-Lys-Lys(Boc)-Phe-NH$_2$:

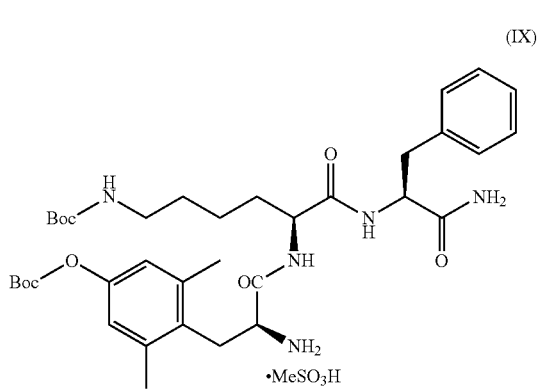

(IV)

and reacting the compound (IV) with hydrogen and methanesulfonic acid (V)

MeSO$_3$H                         (V)

in the presence of a catalyst to obtain the free amine salt (VI) MeSO$_3$H.H-Lys(Boc)-Phe-NH$_2$:

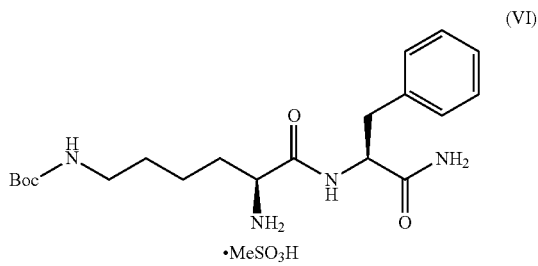 [SMILES: "·MeSO3H" ; CC(C)(C)OC(=O)NCCCC[C@H](N)C(=O)N[C@@H](Cc1ccccc1)C(N)=O]

(VI)

The salt (VI) is reacted with the protected amino acid Z-Dmt(Boc)-OH (VII)

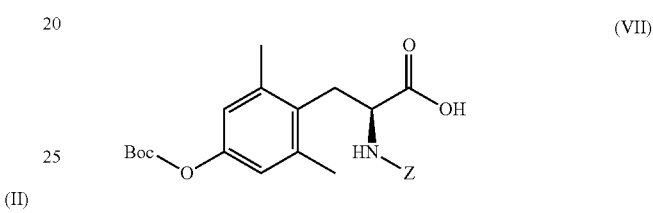

(VII)

to obtain the protected tripeptide Z-Dmt(Boc)-Lys(Boc)-Phe-NH$_2$ (VIII):

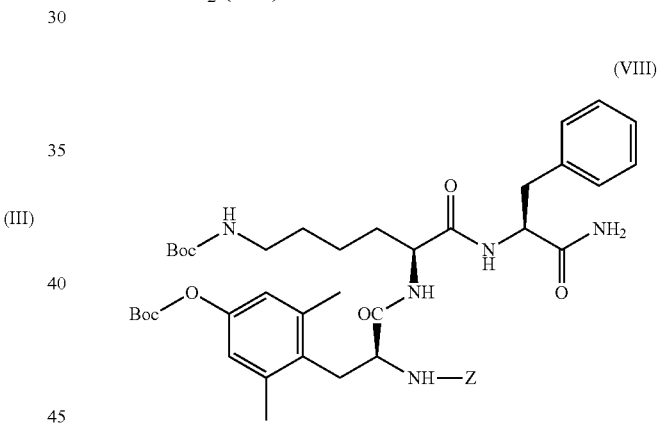

(VIII)

which is treated with hydrogen and methanesulfonic acid (V) to obtain the corresponding salt MeSO$_3$.H-Dmt(Boc)-Lys(Boc)-Phe-NH$_2$ (IX):

(IX)

The acid salt (IX) is coupled with Z-D-Arg-ONa (X)

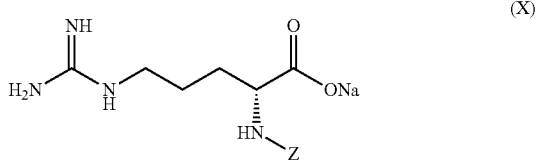

(X)

to form the protected tetrapeptide Boc-D-Arg-Dmt(Boc)-Lys(Boc)-Phe-NH$_2$ (XI):

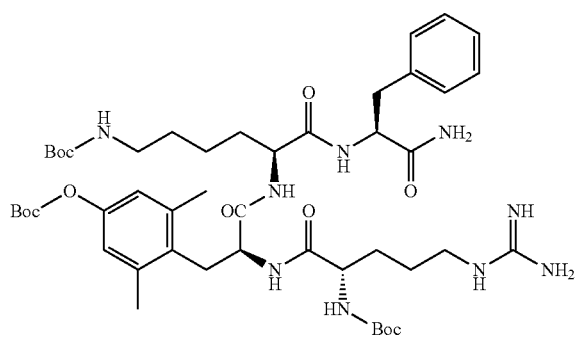

(XI)

The tetrapeptide H-D-Arg-Dmt-Lys-Phe-NH$_2$ (I) is obtained by deprotection and further salt formation with trifluoroacetic acid in solvents of (XI). Deprotection is performed by simple acidolysis of the three Boc groups without use of Pd catalysts which can cause the presence of Pd in the final compound.

The same acidolysis can be performed with other acids such as HCl or HBr, leading to the corresponding salts. This process allows obtaining the peptide as a solid which can be used in formulation as such or can be converted to any other salt if required. The purity of the crude final compound thus obtained is 97% without any additional crystallization and can be easily improved to 99% by selection of the appropriate crystallization mixture.

In one embodiment of the process, the coupling between (II) and (III) is performed in the presence of N,N,N',N'-tetramethyl-O-(benzotriazol-1-yl)uranium tetrafluoroborate (known as TBTU) and an organic base belonging to the class of tertiary amines such as NMM, triethylamine and diisopropylamine as well as polar solvents as NMM, DMF, acetonitrile, tetrahydrofuran (THF), 2-methyl-tetrahydrofuran (2-Me-THF), etc.

In one embodiment, the coupling between (II) and (III) is performed in a temperature range between 0° C. and 60° C., preferably between 20° C. and 30° C.

The hydrogenation of (IV) can be accomplished with various techniques such as homogeneous catalytic hydrogenation, heterogeneous catalytic hydrogenation or catalytic transfer hydrogenation. In a particular embodiment, hydrogenation is performed with hydrogen gas and Pd on carbon as catalyst.

In another embodiment, the formation of methanesulfonic salt (VI) is obtained with methanesulfonic acid (V) in dimethylformamide as solvent and crystallized from the same solvent. Other suitable solvents for crystallization are THF, ethyl acetate and acetonitrile.

In another embodiment, the formation of methanesulfonic salt (IX) is obtained in methylene chloride as solvent and crystallized from the same solvent. Other solvents for crystallization are THF, ethyl acetate and acetonitrile.

In one embodiment of process the coupling reaction between compound (VI) and compound (VII) is performed in the presence of N,N,N',N'-tetramethyl-O-(benzotriazol-1-yl)uranium tetrafluoroborate (TBTU) and an organic base belonging to the class of tertiary amine such as NMM, triethylamine and diisopropylamine as well as polar solvents as NMM, DMF, acetonitrile, THF, 2-Me-THF, etc.

In another embodiment, the hydrogenation of (VIII) can be accomplished with various techniques as homogeneous catalytic hydrogenation, heterogeneous catalytic hydrogenation or catalytic transfer hydrogenation. In a particular embodiment, the hydrogenation is performed with hydrogen gas and Pd on carbon as catalyst.

In another embodiment, the formation of methanesulfonic salt (IX) is obtained with methanesulfonic acid (V) in dimethylformamide as solvent and crystallized from the same solvent. Other solvents for crystallization are THF, ethyl acetate and acetonitrile.

In one embodiment of process the coupling reaction between compound (IX) and compound (X) is performed in the presence of N,N,N',N'-tetramethyl-O-(benzotriazol-1-yl) uranium tetrafluoroborate (known as TBTU) and an organic base belonging to the class of tertiary amine such as NMM, triethylamine and diisopropylamine as well as polar solvents as NMM, DMF, acetonitrile, THF, 2-Me-THF, etc. In one embodiment the deprotection of (XI) is performed with trifluoroacetic acid and solvents. The most appropriate solvents are heptanes, IPA, etc.

In one aspect of the process, the intermediates (IV), (VI), (VIII), (IX) and (XI) are isolated and crystallized. When the intermediates are isolated, their purity exceeds 98%.

In one preferred aspect, the crystallization of intermediate (VIII), Z-Dmt(Boc)-Lys(Boc)-Phe-NH$_2$ is able to avoid the transfer of a critical impurity to the following process steps.

In one preferred aspect the critical impurity is the compound (XII), H-D-Dmt(Boc)-Lys(Boc)-Phe-NH$_2$.

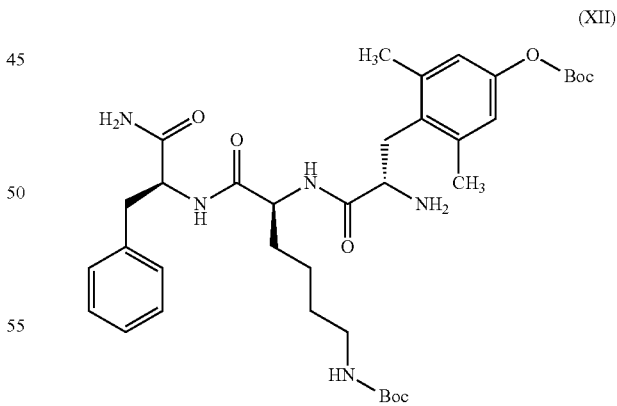

(XII)

In another preferred aspect the crystallization process for the protected tetrapeptide (XI), Boc-D-Arg-Dmt(Boc)-Lys(Boc)-Phe-NH$_2$ allows to obtain the product as a solid with a purity close to 99%.

In another preferred aspect the final deprotection is performed by reaction with trifluoroacetic acid and allows to obtain the final product in crystalline solid form of trifluoroacetate salt after simple crystallization without any need of HPLC purification or any freeze-drying, which are purification and isolation processes extremely expensive but commonly used in the manufacture of peptide as drug.

In a preferred aspect, the process allows to obtain the peptide as a solid which can be used in formulation as such or can be easily converted in any other salt if required. The purity of the final compound thus obtained is 99% and each impurity is approx. 0.2% or below.

EXAMPLES

Example 1: Preparation of Z-Lys(Boc)-Phe-NH$_2$ (IV)

Charge 100 mL of DMF, 9.5 g of H-Phe-NH$_2$, 20 g of Z-Lys(Boc)-OH and 10.6 g of N-methylmorpholine in a flask. Stir the mixture at 20-22° C. for 15 min. Add 18.6 g of TBTU and stir the mixture at room temperature overnight. Add 200 mL of methanol and 250 mL of water into the mixture and stir the mixture at room temperature for 1 h. Filter the mixture to isolate the solid product. Transfer the filter cake into a flask containing 200 mL of methanol. Heat the mixture at refluxing for 1 h, and then cool down to room temperature. Filter the mixture to isolate the solid product. Dry the filter cake at 35-40° C. and under vacuum to obtain 20.5 g of the white solid product.

Example 2: Preparation of MeSO$_3$H.H-Lys(Boc)-Phe-NH$_2$ (VI)

Charge 100 mL of DMF, 12.5 g of 5% Pd/C (60% water content), 10 g of Z-Lys(Boc)-Phe-NH$_2$ and 1.83 g of methanesulfonic acid into a flask. Change the atmosphere of the flask with hydrogen. Stir the mixture at 20-25° C. and under 1 atm hydrogen for 3 h. HPLC analysis shows that all the Z-Lys(Boc)-Phe-NH$_2$ was converted. The resultant mixture was directly used in the next step.

Example 3: Preparation of Z-Dmt(Boc)-Lys(Boc)-Phe-NH$_2$ (VIII)

Charge 8.5 g of Z-Dmt(Boc)-OH and 6.1 g of TBTU into the DMF solution of MeSO$_3$H.H-Lys(Boc)-Phe-NH$_2$ obtained in last step. Stir the mixture at room temperature for 15 min. Cool down the mixture to 10-15° C. Add 5.8 g of N-methylmorpholine slowly while keeping the temperature below 20° C. Stir the mixture at 10-15° C. for 18 h. Filter the mixture to remove the Pd/C catalyst and other precipitates and wash the filter cake with DMF. Combine the filtrate and the washing solution and add 32 mL of methylene chloride into the filtrate. Add the resultant solution into a flask containing 500 mL of water, and then stir the mixture for 20 min. Filter the mixture to isolate the solid product and wash the filter cake with water three times. Transfer the filter cake into a flask containing 450 mL of acetone and heat the mixture to refluxing under stirring. At refluxing and under stirring add 200 mL of hexanes and cool down the mixture to room temperature. Filter the mixture to isolate the solid product. Repeat the previous work-up operations. Dry the resultant filter cake at 40° C. and under vacuum to give 12.4 g of the product.

Example 4: Preparation of MeSO$_3$H.H-Dmt(Boc)-Lys(Boc)-Phe-NH$_2$ (IX)

Charge 12.4 g of Z-Dmt(Boc)-Lys(Boc)-Phe-NH$_2$, 100 mL of DMF, 12.4 g of 5% Pd/C (60% water content) and 1.46 g of methanesulfonic acid into a flask. Change the atmosphere of the flask with hydrogen. Stir the mixture at 20-25° C. and under 1 atm hydrogen for 3 h. HPLC analysis shows that all the Z-Lys(Boc)-Phe-NH$_2$ was converted (HPLC purity 98.1%). The resultant mixture is directly used in the next step.

Example 5: Preparation of Boc-D-Arg-Dmt(Boc)-Lys(Boc)-Phe-NH$_2$ (XI)

Charge 8.5 g of Boc-D-Arg-OH, 8.84 g of TBTU and 9.7 g of N-methylmorpholine into the DMF mixture of H-Dmt(Boc)-Lys(Boc)-Phe-NHe.MeSO$_3$H at room temperature. Stir the mixture at room temperature for 40 h. Filter the mixture to remove the Pd/C and other precipitates. Add 250 mL of ethyl acetate into the filtrate. Wash the organic solution with water (200 mL×4). Concentrate the organic solution at 40-45° C. and under vacuum to remove most of the solvent. Add 100 mL of MTBE to the residue and stir the mixture vigorously at room temperature for 1 h. Filter the mixture to isolate the solid product. Transfer the filter cake into a flask containing 200 mL of ethyl acetate. Heat the mixture at 50-55° C. and under stirring for 3 h, and then cool down to room temperature. Filter the mixture to isolate the solid product. Repeat the previous work-up operations. Dry the filter cake at 40-45° C. and under vacuum to obtain 10.7 g of white solid product. HPLC purity 98.2%.

Example 6: Preparation of H-D-Arg-Dmt-Lys-Phe-NH$_2$ (I), (MTP-131)

Charge 1.0 g and 10 mL TFA in a flask. Stir the mixture at room temperature for 20 min. Add 10 mL of IPA to the reaction mixture. Add the resultant mixture slowly into a flask containing 40 mL of heptane under vigorous stirring. Filter the mixture to isolate the solid product and wash the filter cake with IPA. Dry the filter cake at 40-45° C. and under vacuum to obtain 0.5 g of solid product. Analytical Data: HPLC purity: 96.6%.

The invention claimed is:

1. A liquid-phase process for the production of H-D-Arg-(2,6-Dimethyl)Tyr-Lys-Phe-NH2 of formula (I), in the form of the trifluoroacetic acid salt,

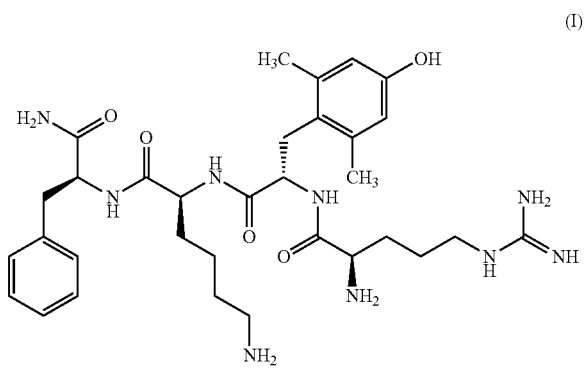 [SMILES: Cc1cc(O)cc(C)c1C[C@H](NC(=O)[C@H](N)CCCNC(=N)N)C(=O)N[C@@H](CCCCN)C(=O)N[C@@H](Cc1ccccc1)C(N)=O]

which comprises the following steps:

coupling compound (II) H-Phe-NH2:

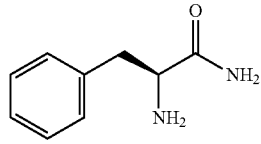
(II)

with compound (III) Z-Lys(Boc)-OH:

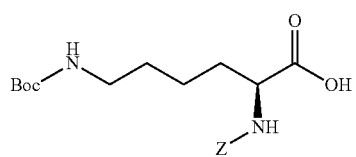
(III)

to obtain a compound of formula (IV), Z-Lys(Boc)-Phe-NH2:

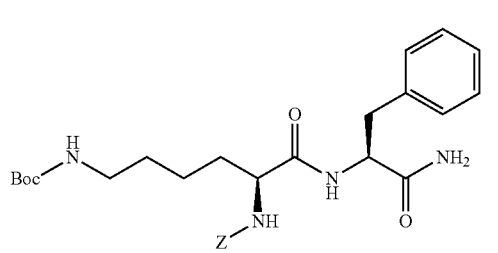
(IV)

reacting compound (IV) with hydrogen and methane-sulfonic acid (V)

MeSO3H   (V)

in the presence of a catalyst to obtain the free amine salt (VI) MeSO3H.H-Lys(Boc)-Phe-NH2:

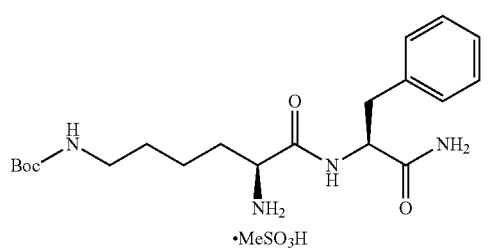
(VI)

reacting salt (VI) with the protected amino acid Z-Dmt(Boc)-OH (VII)

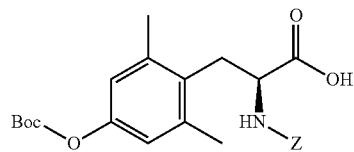
(VII)

to obtain the protected tripeptide Z-Dmt(Boc)-Lys(Boc)-Phe-NH2 (VIII):

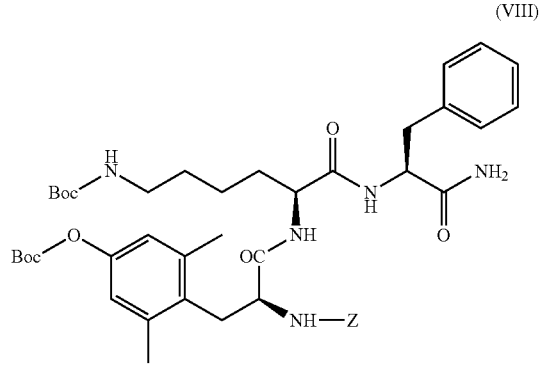
(VIII)

treating compound (VIII) with hydrogen and methane-sulfonic acid (V) to obtain the corresponding salt MeSO3.H-Dmt(Boc)-Lys(Boc)-Phe-NH2 (IX):

(IX)

coupling the acid salt (IX) with Z-D-Arg-ONa (X)

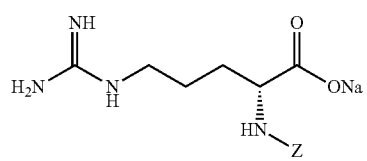
(X)

to form the protected tetrapeptide Boc-D-Arg-Dmt(Boc)-Lys(Boc)-Phe-NH2 (XI):

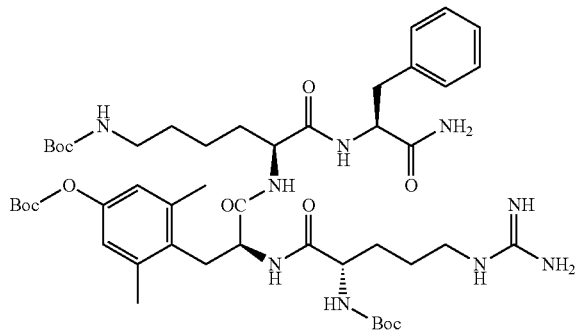

(XI)

deprotecting compound (XI) to obtain the tetrapeptide H-D-Arg-Dmt-Lys-Phe-NH2 (I) and further salifying it with trifluoroacetic acid in solvents.

2. A process according to claim 1 wherein the deprotection is performed by simultaneous acidolysis of the three Boc groups with organic acids.

3. A process according to claim 1 wherein the deprotection is performed by simultaneously acidolysis of the three Boc group with trifluoroacetic acid, without use of Pd catalysts.

4. A process according the claim 1 wherein the acidolysis can be performed with other acids such as HCl or HBr, leading to the corresponding salts.

5. A process according to claim 1 wherein the final product (I) is obtained in solid crystalline form of the trifluoroacetate salt after simple crystallization without any need of HPLC purification or any freeze-drying.

6. A process according the claim 1 wherein the coupling between (II) and (III) is performed in the presence of N,N,N',N'-tetramethyl-O-(benzotriazol-1-yl)uranium tetrafluoroborate (known as TBTU) and polar solvents such as NMP, DMF, acetonitrile, DMSO and THF.

7. A process according the claim 1 wherein coupling between (II) and (III) is performed in a temperature range between −10° C. and 50° C.

8. A process according the claim 1 wherein formation of methanesulfonic salt (VI) is obtained in methanol, NMP, acetonitrile or THF as solvent and crystallized from the same solvent.

9. A process according to claim 1 wherein the coupling reaction between compound (IX) and compound (X) is performed in the presence of N,N,N',N'-tetramethyl-O-(benzotriazol-1-yl)uranium tetrafluoroborate (TBTU) and polar solvents selected from NMP, DMF, acetonitrile, DMSO and THF.

10. A compound of formula (VIII) Z-(2,6-dimethyl)Tyr(Boc)-Lys(Boc)-Phe-NH2

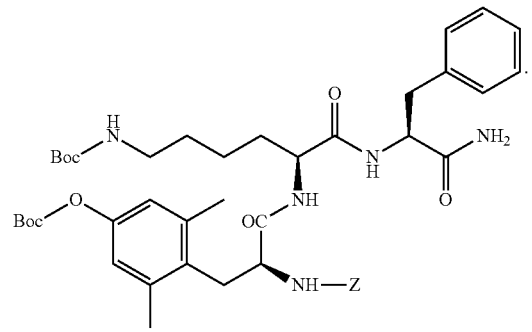

(VIII)

11. A compound of formula (XIV) H-(2,6-dimethyl)Tyr(Boc)-Lys(Boc)-Phe-NH2 or a salt thereof:

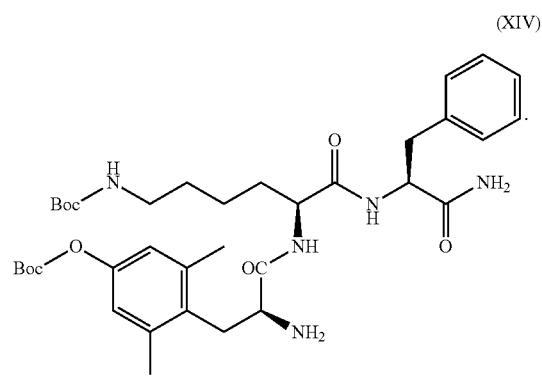

(XIV)

12. A compound of formula (XI) Boc-D-Arg-(2,6-dimethyl)Tyr(Boc)-Lys(Boc)-Phe-NH2:

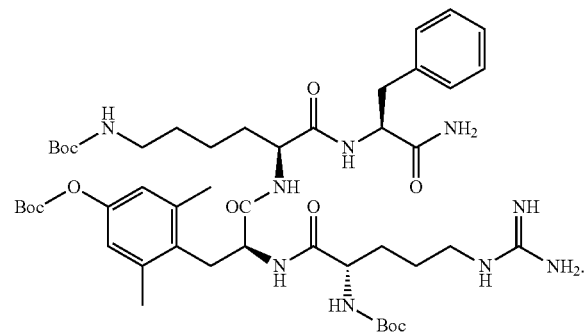

(XI)

* * * * *